US010085866B2

(12) United States Patent
Wojcik et al.

(10) Patent No.: US 10,085,866 B2
(45) Date of Patent: Oct. 2, 2018

(54) APPARATUS AND METHOD FOR DRAINING MATERIAL FROM A STOMACH

(71) Applicant: Aspire Bariatrics, Inc., Wilmington, DE (US)

(72) Inventors: Steven E. Wojcik, Shoreline, WA (US); Sean O'Connor, Westchester, PA (US); Kusal Das, Wrightstown, PA (US)

(73) Assignee: Aspire Bariatrics, Inc., Wilmington, DE (US)

( * ) Notice: Subject to any disclaimer, the term of this patent is extended or adjusted under 35 U.S.C. 154(b) by 137 days.

(21) Appl. No.: 14/769,243

(22) PCT Filed: Feb. 21, 2014

(86) PCT No.: PCT/US2014/017546
§ 371 (c)(1),
(2) Date: Aug. 20, 2015

(87) PCT Pub. No.: WO2014/130757
PCT Pub. Date: Aug. 28, 2014

(65) Prior Publication Data
US 2015/0366692 A1 Dec. 24, 2015

Related U.S. Application Data

(60) Provisional application No. 61/768,462, filed on Feb. 23, 2013.

(51) Int. Cl.
*A61F 5/00* (2006.01)
*A61M 1/00* (2006.01)
(Continued)

(52) U.S. Cl.
CPC ......... *A61F 5/0076* (2013.01); *A61M 1/0021* (2013.01); *A61M 1/0058* (2013.01);
(Continued)

(58) Field of Classification Search
CPC . A61F 5/0076; A61M 1/0021; A61M 1/0058; A61M 39/1011; A61M 39/105;
(Continued)

(56) References Cited

U.S. PATENT DOCUMENTS 2,533,915 A  12/1950  Brooks
2,933,140 A   4/1960  Gagliardo
(Continued)

FOREIGN PATENT DOCUMENTS

DE   10239443   3/2004
EP    0059044   9/1982
(Continued)

OTHER PUBLICATIONS

Annex to form PCT/ISA/206 Communication Relating to the Results of the Partial International Search for International Application No. PCT/US2007/015479 dated Dec. 7, 2007, 2 pages.
(Continued)

*Primary Examiner* — Benjamin Klein
(74) *Attorney, Agent, or Firm* — Baker & Hostetler LLP

(57) ABSTRACT

This invention relates to new apparatuses for draining material from a stomach and infusing fluid into the stomach comprising a tubing connector, a housing unit, and a one-way valve. In an embodiment the connector can have a first port, a second port, a third port and a branched lumen that extends through each of the first, second and third ports. The housing unit can have a housing lumen that is sized and shaped to receive the third port and the housing unit is sized and shaped to receive the connector. The one-way valve can be sized and shaped to be received in the housing lumen.

15 Claims, 7 Drawing Sheets

(51) Int. Cl.
  *A61M 39/24* (2006.01)
  *B08B 9/032* (2006.01)
  *A61M 3/02* (2006.01)
  *A61M 39/10* (2006.01)

(52) U.S. Cl.
  CPC .......... *A61M 39/105* (2013.01); *A61M 39/24* (2013.01); *B08B 9/0321* (2013.01); *A61M 3/0262* (2013.01); *A61M 39/1011* (2013.01); *A61M 2039/1044* (2013.01); *A61M 2039/2466* (2013.01); *A61M 2207/00* (2013.01); *A61M 2209/088* (2013.01); *A61M 2209/10* (2013.01); *A61M 2210/1053* (2013.01); *Y10T 29/49828* (2015.01)

(58) Field of Classification Search
  CPC .............. A61M 39/24; A61M 2207/00; A61M 2209/088; A61M 2209/10; A61M 2210/1053; A61M 2039/1011; A61M 2039/1044; A61M 2039/2466; A61M 3/0262
  See application file for complete search history.

(56) References Cited

U.S. PATENT DOCUMENTS

| | | |
|---|---|---|
| 3,144,866 A | 8/1961 | Ellis |
| 3,066,672 A | 12/1962 | Crosby, Jr. |
| 3,144,868 A | 8/1964 | Jascalevich |
| 3,214,069 A | 10/1965 | Dike |
| 3,232,578 A | 2/1966 | Cousins |
| 3,384,342 A | 5/1968 | Passer |
| 3,506,237 A | 4/1970 | Tometsko |
| 3,598,150 A | 8/1971 | Nolan |
| 3,752,158 A | 8/1973 | Kariher |
| 3,860,000 A | 1/1975 | Wootten et al. |
| 3,884,808 A | 5/1975 | Scott |
| 3,924,625 A | 12/1975 | Peterson |
| 4,082,095 A | 4/1978 | Mendelson et al. |
| 4,116,589 A | 9/1978 | Rigston |
| 4,189,795 A | 2/1980 | Conti et al. |
| 4,190,173 A | 2/1980 | Mason et al. |
| 4,315,509 A | 2/1982 | Smit |
| 4,315,513 A | 2/1982 | Nawash et al. |
| 4,344,435 A | 8/1982 | Aubin |
| 4,356,824 A | 11/1982 | Vazuez |
| 4,381,765 A | 5/1983 | Burton |
| 4,393,873 A | 7/1983 | Nawash et al. |
| 4,393,875 A | 7/1983 | Nawash et al. |
| 4,449,972 A | 5/1984 | Kruger |
| 4,464,175 A | 8/1984 | Altman et al. |
| 4,525,156 A | 6/1985 | Benusa et al. |
| 4,538,653 A | 9/1985 | Shea et al. |
| 4,551,130 A | 11/1985 | Herbert et al. |
| 4,553,960 A | 11/1985 | Lazarus et al. |
| 4,555,242 A | 11/1985 | Saudagar |
| 4,642,092 A | 2/1987 | Moss |
| 4,668,225 A | 5/1987 | Russo et al. |
| 4,685,901 A | 8/1987 | Parks |
| 4,723,547 A | 2/1988 | Kullas et al. |
| 4,790,812 A | 12/1988 | Hawkins, Jr. et al. |
| 4,804,375 A | 2/1989 | Robertson |
| 4,822,338 A | 4/1989 | Longmore et al. |
| 4,834,724 A | 5/1989 | Geiss |
| 4,863,438 A | 9/1989 | Gauderer et al. |
| 4,899,747 A | 2/1990 | Garren et al. |
| 4,935,009 A | 6/1990 | Calwell et al. |
| 5,071,405 A | 12/1991 | Piontek et al. |
| 5,074,850 A | 12/1991 | Chion |
| 5,098,378 A | 3/1992 | Piontek et al. |
| 5,234,454 A | 8/1993 | Bangs |
| 5,259,399 A | 11/1993 | Brown |
| 5,263,367 A | 11/1993 | Pippert |
| 5,306,300 A | 4/1994 | Berry |
| 5,345,949 A | 9/1994 | Shlain |
| 5,358,488 A | 10/1994 | Suriyapa |
| 5,379,926 A | 1/1995 | Mueller et al. |
| 5,411,022 A | 2/1995 | McCue et al. |
| 5,417,644 A | 5/1995 | Felix et al. |
| 5,451,215 A | 9/1995 | Wolter |
| 5,468,240 A | 11/1995 | Gentelia et al. |
| 5,507,419 A | 4/1996 | Martin et al. |
| 5,520,307 A | 5/1996 | Miller et al. |
| 5,520,634 A | 5/1996 | Fox et al. |
| 5,520,662 A | 5/1996 | Moss |
| 5,527,280 A | 6/1996 | Goelz |
| 5,549,657 A | 8/1996 | Stern et al. |
| 5,601,213 A | 2/1997 | Daniello |
| 5,601,604 A | 2/1997 | Vincent |
| 5,618,296 A | 4/1997 | Sorensen et al. |
| 5,716,347 A | 2/1998 | Gibbs et al. |
| 5,727,555 A | 3/1998 | Chait |
| 5,730,322 A | 3/1998 | Iba et al. |
| 5,741,287 A | 4/1998 | Alden et al. |
| 5,743,468 A | 4/1998 | Laidler |
| 5,868,141 A | 2/1999 | Ellias |
| 5,871,475 A | 2/1999 | Frassica |
| 5,890,517 A * | 4/1999 | Laible .................... F16L 37/22 137/614 |
| 5,895,373 A | 4/1999 | Hirsch |
| 5,895,377 A | 4/1999 | Smith et al. |
| 5,897,530 A | 4/1999 | Jackson |
| 5,925,075 A | 7/1999 | Myers et al. |
| 5,927,604 A | 7/1999 | Laidler |
| 5,972,399 A | 10/1999 | Lapre et al. |
| 5,989,231 A | 11/1999 | Snow et al. |
| 6,019,746 A | 2/2000 | Picha et al. |
| 6,039,251 A | 3/2000 | Holowko et al. |
| 6,048,329 A | 4/2000 | Thompson et al. |
| 6,077,243 A | 6/2000 | Quinn |
| 6,077,250 A | 6/2000 | Snow et al. |
| 6,152,911 A | 11/2000 | Gainnoble |
| 6,210,347 B1 | 4/2001 | Forsell |
| 6,245,039 B1 | 6/2001 | Brugger et al. |
| 6,315,170 B1 | 11/2001 | Thomson et al. |
| 6,322,495 B1 | 11/2001 | Snow et al. |
| 6,328,720 B1 | 12/2001 | McNally et al. |
| 6,341,737 B1 | 1/2002 | Chang |
| 6,381,495 B1 | 4/2002 | Jenkins |
| 6,447,472 B1 | 9/2002 | Moss |
| 6,453,907 B1 | 9/2002 | Forsell |
| 6,454,785 B2 | 9/2002 | De Hoyos Garza |
| 6,506,179 B1 | 1/2003 | Tiefenthal et al. |
| 6,511,490 B2 | 1/2003 | Robert |
| 6,533,734 B1 | 3/2003 | Corley et al. |
| 6,572,629 B2 | 6/2003 | Kalloo et al. |
| 6,579,301 B1 | 6/2003 | Bales et al. |
| 6,585,681 B2 | 7/2003 | Brugger et al. |
| 6,615,084 B1 | 9/2003 | Cigaina |
| 6,626,884 B1 | 9/2003 | Dillon et al. |
| 6,627,206 B2 | 9/2003 | Lloyd |
| 6,645,183 B2 | 11/2003 | Christensen et al. |
| 6,659,974 B1 | 12/2003 | Moss |
| 6,666,853 B2 | 12/2003 | Chu et al. |
| 6,691,981 B1 | 2/2004 | Hart |
| 6,699,233 B2 | 3/2004 | Slanda et al. |
| 6,736,336 B2 | 5/2004 | Wong |
| 6,743,193 B2 | 6/2004 | Brugger et al. |
| 6,752,790 B2 | 6/2004 | Coombs |
| 6,755,869 B2 | 6/2004 | Geitz |
| 6,757,957 B2 | 7/2004 | McClean et al. |
| 6,758,836 B2 | 7/2004 | Zawacki |
| 6,902,541 B2 | 6/2005 | McNally et al. |
| 6,921,389 B2 | 7/2005 | Scagliarini et al. |
| 6,923,786 B2 | 8/2005 | Rouns et al. |
| 6,976,980 B2 | 12/2005 | Brenner et al. |
| 7,025,791 B2 | 4/2006 | Levine et al. |
| 7,066,917 B2 | 6/2006 | Talamonti |
| 7,174,916 B2 | 2/2007 | Chang |
| 7,175,612 B2 | 2/2007 | Felix et al. |
| 7,383,852 B2 | 6/2008 | Pittaway et al. |
| 7,434,594 B1 | 10/2008 | Robbins et al. |
| 7,524,445 B2 | 4/2009 | Duran et al. |

(56) References Cited

U.S. PATENT DOCUMENTS

| | | | |
|---|---|---|---|
| 7,641,648 B2 | 1/2010 | Bouphavichith et al. |
| 7,648,479 B2 | 1/2010 | Solovay et al. |
| 7,682,346 B2 | 3/2010 | McNally et al. |
| 7,708,724 B2 | 5/2010 | Weston |
| 7,713,246 B2 | 5/2010 | Shia et al. |
| 7,740,624 B2 | 6/2010 | Klein et al. |
| 7,815,629 B2 | 10/2010 | Klein et al. |
| 8,002,727 B2 | 8/2011 | Brugger et al. |
| 8,002,758 B2 | 8/2011 | Kamen et al. |
| 8,062,285 B2 | 11/2011 | Langloss et al. |
| 8,282,623 B2 | 10/2012 | Klein et al. |
| 2001/0049490 A1 | 12/2001 | Slanda |
| 2002/0077604 A1 | 6/2002 | Willis et al. |
| 2002/0115966 A1 | 8/2002 | Christensen et al. |
| 2002/0193753 A1 | 12/2002 | Rouns et al. |
| 2003/0032932 A1 | 2/2003 | Stout |
| 2003/0040808 A1 | 2/2003 | Stack et al. |
| 2003/0069553 A1 | 4/2003 | Talamonti |
| 2003/0109935 A1 | 6/2003 | Geitz |
| 2003/0149395 A1 | 8/2003 | Zawaki |
| 2003/0158539 A1 | 8/2003 | Bouphavichith et al. |
| 2003/0208113 A1 | 11/2003 | Mault et al. |
| 2003/0225369 A1 | 12/2003 | McMichael |
| 2004/0055948 A1 | 3/2004 | Blum et al. |
| 2004/0082909 A1 | 4/2004 | Shia et al. |
| 2004/0167478 A1 | 8/2004 | Mooney et al. |
| 2004/0220516 A1 | 11/2004 | Solomon et al. |
| 2005/0107743 A1 | 5/2005 | Fangrow, Jr. |
| 2005/0277900 A1 | 12/2005 | Klein et al. |
| 2005/0283130 A1 | 12/2005 | Klein et al. |
| 2006/0079853 A1 | 4/2006 | Christensen et al. |
| 2006/0129092 A1 | 6/2006 | Hanlon |
| 2006/0135914 A1 | 6/2006 | Chu et al. |
| 2006/0147665 A1 | 7/2006 | Duran et al. |
| 2006/0264983 A1 | 11/2006 | Holsten et al. |
| 2006/0270970 A1 | 11/2006 | Moss |
| 2006/0289011 A1 | 12/2006 | Helsel |
| 2007/0187406 A1 | 8/2007 | Nobile et al. |
| 2008/0033364 A1* | 2/2008 | Kamen ............... A61F 5/0076 604/173 |
| 2008/0091146 A1 | 4/2008 | Solovay et al. |
| 2009/0247961 A1* | 10/2009 | Carlyon ............... A61M 5/28 604/237 |
| 2010/0106130 A1 | 4/2010 | Solovay et al. |
| 2010/0106131 A1 | 4/2010 | Klein et al. |
| 2010/0241090 A1 | 9/2010 | Klein et al. |
| 2011/0082442 A1 | 4/2011 | Solovay et al. |
| 2011/0098660 A1 | 4/2011 | Porreca |
| 2011/0178480 A1 | 7/2011 | Solovay et al. |
| 2011/0190719 A1 | 8/2011 | Kamen et al. |
| 2011/0245771 A1 | 10/2011 | Daly |
| 2013/0204210 A1* | 8/2013 | Pratt ............... A61M 1/0031 604/290 |

FOREIGN PATENT DOCUMENTS

| | | |
|---|---|---|
| EP | 0194980 | 9/1986 |
| EP | 0691868 | 6/2002 |
| EP | 1374930 A1 | 1/2004 |
| EP | 2389962 | 11/2011 |
| EP | 2412393 | 2/2012 |
| FR | 2630011 | 10/1989 |
| GB | 1161436 | 8/1969 |
| JP | S56-131864 | 10/1981 |
| JP | S57-171193 | 10/1982 |
| JP | 62/224358 | 10/1987 |
| JP | 03/18378 | 1/1991 |
| JP | 04-002361 | 1/1992 |
| JP | 04-198680 | 1/1992 |
| JP | 05-115429 | 5/1993 |
| JP | 05-317325 | 12/1993 |
| JP | 07-096030 | 4/1995 |
| JP | 08-196621 | 8/1996 |
| JP | 08-266546 | 10/1996 |
| JP | 2001/29434 | 2/2001 |
| JP | 2003-512121 A | 4/2003 |
| JP | 2005-522269 | 7/2005 |
| JP | 2006-508711 | 3/2006 |
| JP | 2006-102539 | 4/2006 |
| JP | 2009-542349 | 12/2009 |
| JP | 2009-545383 | 12/2009 |
| WO | WO 94/15655 | 7/1994 |
| WO | WO 99/25418 | 5/1999 |
| WO | WO 01/30242 A1 | 5/2001 |
| WO | WO 2001/68007 A1 | 9/2001 |
| WO | WO 2002/32477 | 4/2002 |
| WO | WO 03/086247 | 10/2003 |
| WO | WO 2004/098692 | 11/2004 |
| WO | WO 2005/060869 | 7/2005 |
| WO | WO 2006/014496 | 2/2006 |
| WO | WO 2006/020441 | 2/2006 |
| WO | WO 2006/022709 | 3/2006 |
| WO | WO 2006/088419 | 8/2006 |
| WO | WO 2008/005496 | 1/2008 |
| WO | WO 2008/018082 A2 | 2/2008 |
| WO | WO 2008/019082 | 2/2008 |
| WO | WO 2011/031679 | 3/2011 |

OTHER PUBLICATIONS

Brolin, "Bariatric surgery and long-term control of morbid obesity", JAMA, Dec. 2002, 288(22), 2793-2796.
Buchwald et al., "Bariatric Surgery, a Systematic Review and Meta-Analysis", JAMA, Oct. 13, 2004, 292(14), 1724-1737.
Cantor et al., "Animal Models of Human Psychology", Animals' Agenda, 1997 (Book Review), 18(3), 1 page.
Doenz et al., "Versatility of the Proximal Cope Loop Catheter", American Journal of Roentgenolog, Jan. 1989, 152, 1 page.
Duszak, "Percutaneous Gastrostomy and Jejunostomy", eMedicine Instant access to the Minds of Medicine, http://www.emedicine.com/radio/topic798.htm Jul. 8, 2005, 18 pages.
European Patent Application No. EP 11179953: Extended European Search Report dated Jan. 20, 2012, 7 pages.
Felsher et al., "Decompressive Percutaneous Endoscopic Gastrotomy in Nonmalignant Disease", The American Journal of Surgery, 2004, 187, 254-256.
Flegal et al., "Prevalence and Trends in Obesity Among US Adults, 1999-2000", JAMA, Oct. 9, 2002, 288(1), 1723-1727.
Gehman et al., "Percutaneous Gastrojejunostomy with a Modified Cope Loop Catheter", American Journal of Roentgenology, Jul. 1990, 155, 79-80.
Goldstein, "Beneficial Health Effects of Modest Weight Loss", International Journal of Obesity and Related Metabolic Disorders: Journal of the International Association for the Study of Obesity, Jun. 1992, 16(6), 397-415.
Gray et al., "Modified Catheter for Percutaneous Gastrojejunostomy", Radiology, Oct. 1989, 173(1), 276-278.
Harper et al., "The Long Term Outcome in Crohn's Disease", Am. Soc. Gastrointestinal Endoscopy, Mar. 1987, 30(3), 174-179.
International Patent Application No. PCT/US2012/051995: International Search Report and Written Opinion dated Apr. 12, 2013, 22 pages.
International Patent Application No. PCT/US2014/017546: International Search Report and Written Opinion dated May 14, 2014, 13 pages.
Japanese Application No. 2009-518367: Notice of Reasons for Rejection dated May 15, 2012, 5 pages (English Translation Attached).
Japanese Application No. 2009-522889: Notice of Reasons for Rejection dated May 22, 2012, 7 pages (English Translation Attached).
Japanese Patent Application No. 2012-232652: Notice of Reason for Rejection dated Sep. 8, 2014, 3 Pages.
Lawrence et al., "Percutaneous Endoscopic Gastrostomy for Decompression of the Stomach and Small bowels", Gastrointestinal Endoscopy, 1992, 38(3), 314-318.
Lorentzen et al., "Percutaneous Gastrostomy guided by Ultrasound and Fluoroscopy", ACTA Radiologica, 1995, 3, 159-162.
Luck et al., "Laparoscopic Gastrostomy: Towards the Ideal Technique", Aust. N.Z. J. Surg., 1998, 68, 281-283.

(56) References Cited

OTHER PUBLICATIONS

Meissner, "Adjuvant Surgical Decompression Gastrostomy: Audit of a Procedure Coming of Age", Hepatogastroenterology, Mar.-Apr. 2004, 51(56), 462-464.

Michaud et al., "Gastrostomy as a Decompression Technique in Children with Chronic Gastrointestinal Obstruction", J. Pediatr. Gastroenterol Nutr., Jan. 2001, 32(1), 82-85.

Nassif, "Efficient Decompression and Immediate Enteral Hyperaliment via Gastrostomy as an Adjunct to Gastroplasty", Obes Surg., Mar. 1991, 1(1), 99-102.

Ozmen et al., "Percutaneous Radiological Gastrostomy", European Journal of Radiology, Sep. 2002, 43(3), 186-195.

Pearce et al., "The 'cut and push' Method of Percutaneous Endoscopic Gastrostomy Tube Removal", Clinical Nutrition, 2000, 19(2),133-135.

Shapiro, "Animal Models of Human Psychology: Critique of Science, Ethics, and Policy", Seattle: Hogrefe and Huber, 1998, Chapter 4, 111-211.

Shike "Percutaneous Endoscopic Stomas for Enteral Feeding and Drainage", Oncology (Huntingt), Jan. 1995, 9(1), 39-44.

Shike et al., "An Active Esophageal Prosthesis", Gastrointestinal Endoscopy, Jan. 1995, 41(1), 64-67.

Shike et al., "Combined Gastric Drainage and Jejunal feeding through a Percutaneous Endoscopic Stoma", Gastrointestinal Endoscopy, May-Jun. 1990, 36(3), 290-292.

Shike et al., "External Biliary Duodenal Drainage through a Percutaneous Endoscopic Duodensotomy", Gastrointestinal Endoscopy, 1989, 35(2), 104-105.

Shike et al., "Skin-level Gastrostomies and Jejunostomies for Long-Term Enter Feeding", JPEN J Parenter Enteral Nurt., Nov.-Dec. 1989, 13(6), 648-650.

Shike, "Percutaneous Endoscopic Gastrostomy and Jejunostomy for long-term feeding in Patients with Cancer of the head and neck", Otolaryngology Head and Neck Surgery, Nov. 1989, 101(5), 549-554.

Suazo-Barahona et al., "Obesity: A Risk Factor for Severe Acute Biliary and Alcoholic Pancreatitis". Am. J. Gastroenterology, Aug. 1998 98(3), 1324-1328.

Thornton et al., "Percutaneous Radiological Gastrostomy with and without T-Fastner Gastropexy: A Randomized Comparison Study", Cardiovasc Interventional Radiology, Nov.-Dec. 2002, 25(6), 467-471.

Wood, M.F. et al, Micropouch gastric bypass: indications for gastrostomy tube placement in the bypassed stomach. Obes Surg. Oct. 2000;10(5):413-9.

\* cited by examiner

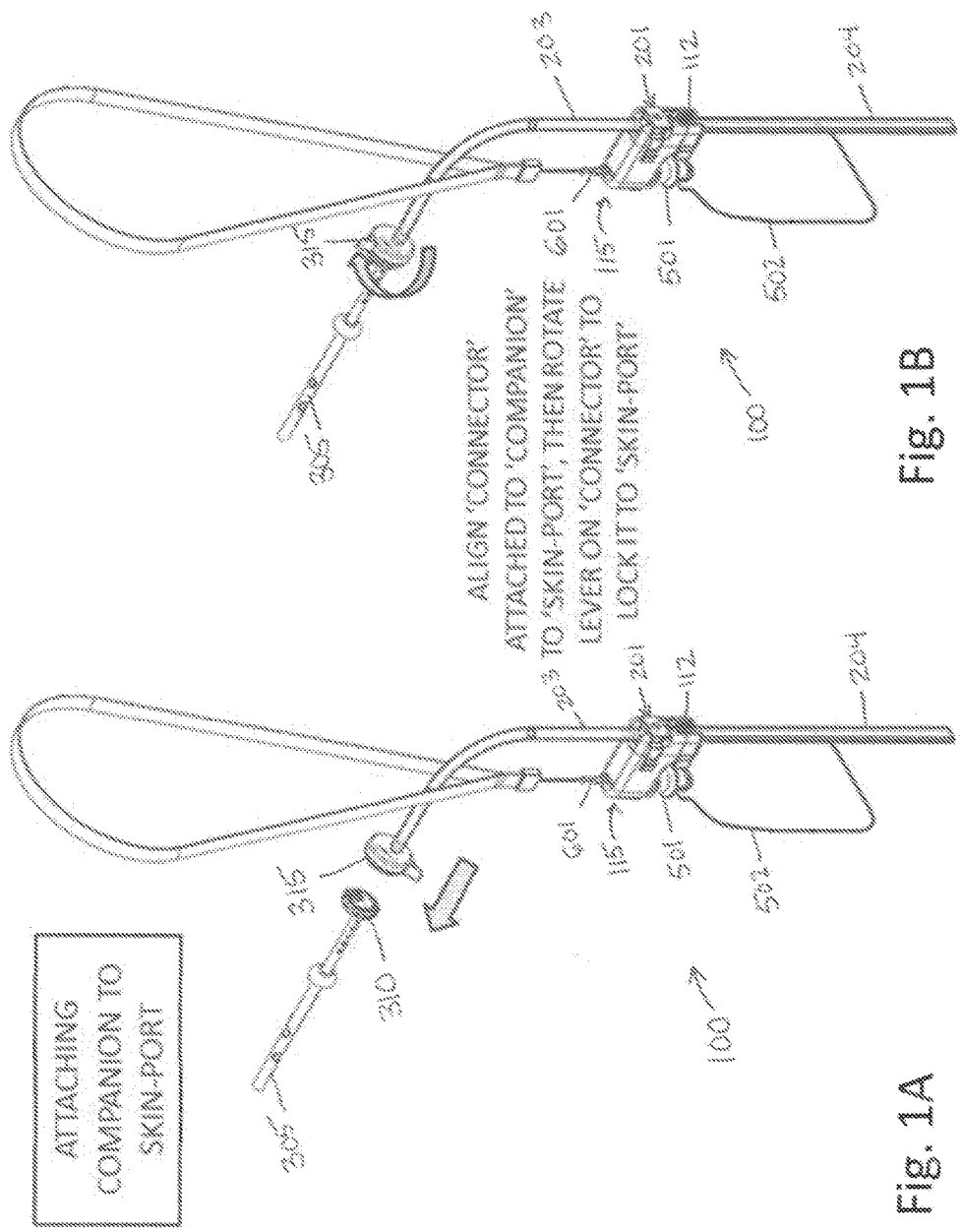

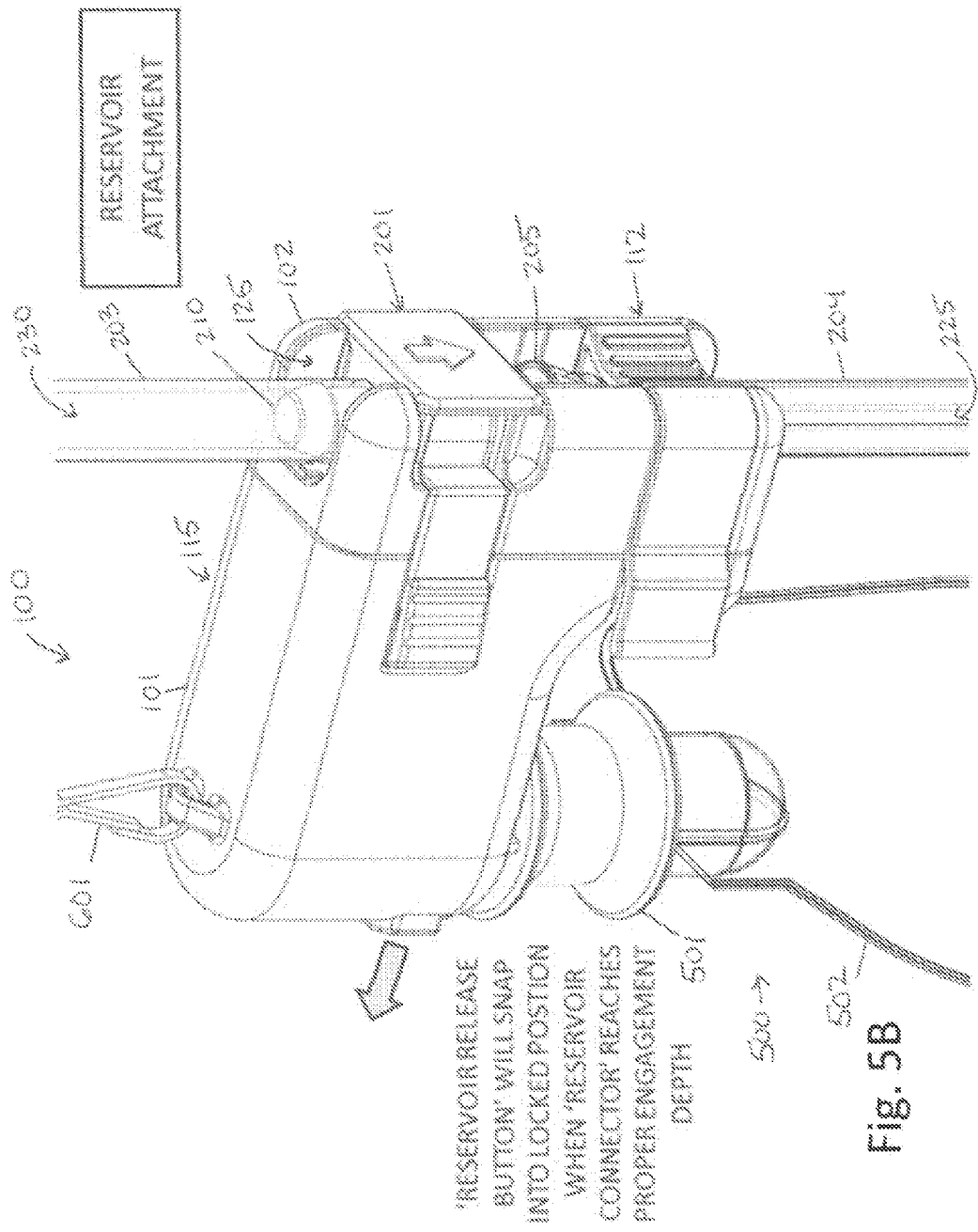

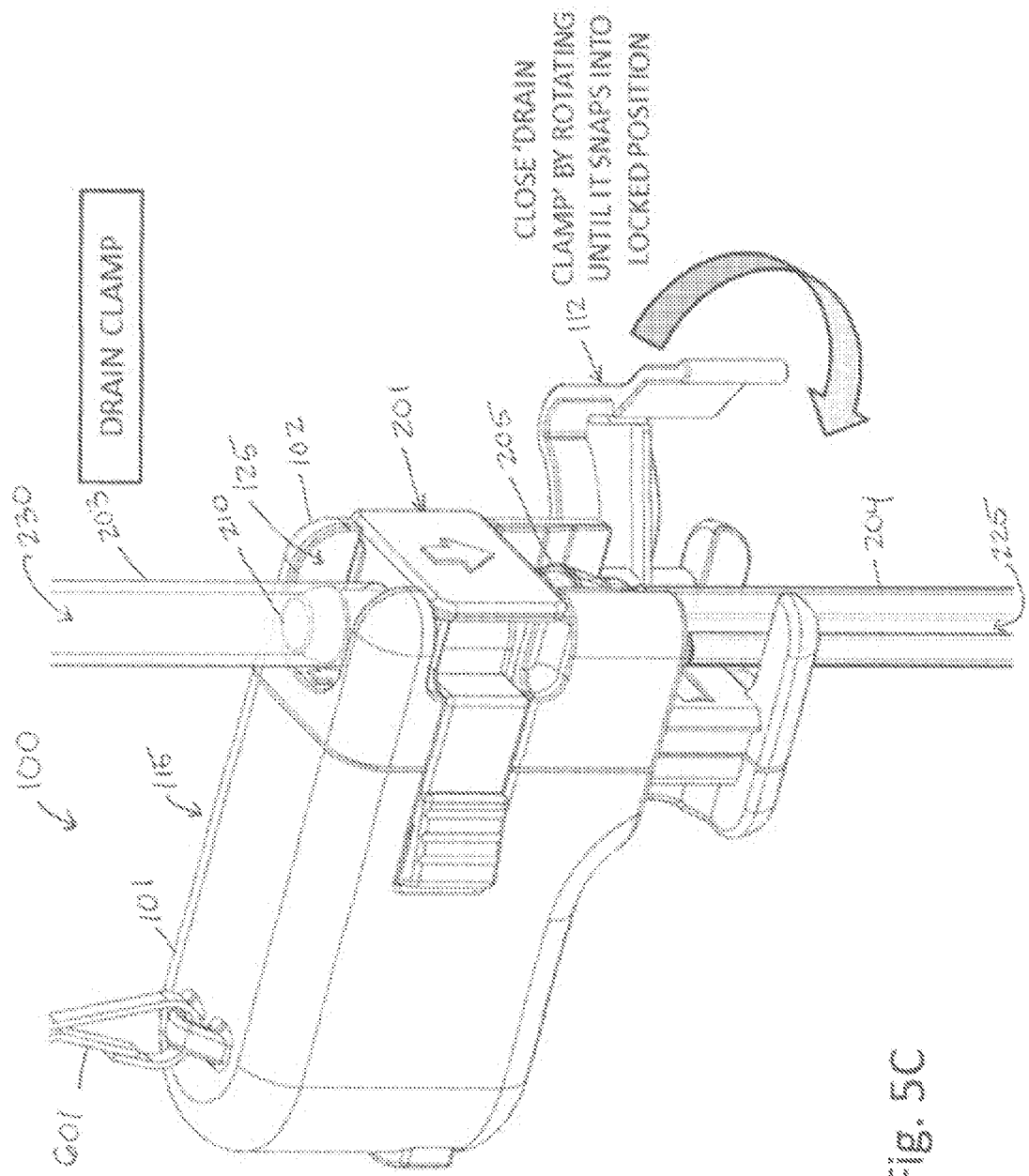

APPARATUS AND METHOD FOR DRAINING MATERIAL FROM A STOMACH

CROSS-REFERENCE TO RELATED APPLICATIONS

This application is the National Stage of International Application No. PCT/US2014/017546 filed Feb. 21, 2014, which claims the benefit of U.S. Provisional Application No. 61/768,462, filed Feb. 23, 2013, the entire disclosures of which are incorporated herein by reference.

TECHNICAL FIELD

The invention generally relates to removal of ingested material from a stomach.

BACKGROUND

Obesity is a major health problem in the United States and other countries. The National Health and Nutrition Examination Survey (1988-1994) reported that approximately 20-25% of Americans are obese, while another study estimated the percentage of overweight Americans to be between 60% and 65% (Flegal K M, Carroll M D, Ogden C L, Johnson C L "Prevalence and trends in obesity among US adults, 1999-2000" JAMA 2002; 288:1723-1727). Obesity can cause numerous health problems, including diabetes, degenerative joint disease, hypertension, and heart disease. Weight reduction can be achieved by increased caloric expenditure through exercise and/or by reduced caloric consumption through diet. However, in most cases, weight gain often recurs and improvements in related co-morbidities are often not sustained.

Surgical procedures present an increasingly common solution for obese patients. Surgical procedures include, for example, stapled gastroplasty, banded gastroplasty, gastric banding, gastric bypass surgery, and bilopancreatic bypass. However, these surgical procedures are invasive, risky and expensive to perform, and many patients regain a substantial portion of the lost weight.

The use of a gastrostomy to drain a portion of ingested food is an alternative to these procedures for weight loss management. Upon installation, one end of the gastrostomy tube will reside within the stomach with the other end passing through the abdominal wall outside of the body. A low-profile valve which rests against the surface of the skin of the abdomen is typically fitted to the external end of the gastrostomy tube to prevent the inadvertent discharge of the contents of the stomach and to prevent inadvertent pulling of the tube inside the stomach.

Typically a fluid, such as water is infused into the stomach to improve the flow of partially digested material out of the stomach through the gastrostomy tube. While a simple drain tube may be connected to the external end of the gastrostomy tube to partially drain the contents of the stomach after a meal therefore reducing the amount of food which is digested, in practice, this simple approach is unsatisfactory. Often, less than the desired portion of the ingested food can be drained before the gastrostomy tube clogs with partially digested food. In practice, a fluid, typically water, is infused through the discharge end of the gastrostomy tube to clear any clogs and further dilute the contents of the stomach so that additional partially digested food may be drained.

Various devices have been used to allow the user to alternately switch between draining the stomach, unclogging the gastrostomy tube, or diluting the contents of the stomach more quickly and efficiently without disconnecting the drain tube. However, the devices described in prior art for draining material from the stomach and infusing fluid into the stomach allow the drained material from the stomach to pass directly through the apparatus. This makes it difficult to thoroughly clean the malodorous stomach discharge from the apparatus. It also makes it difficult to visually identify a clog within the apparatus itself. Additionally, it is desirable that the process of clearing a clogged gastrostomy tube and diluting the partially digested food can be performed quickly with little physical exertion. The present invention is directed to overcoming some of these deficiencies.

SUMMARY

In one embodiment, an apparatus for draining material from a stomach and infusing fluid into the stomach comprises a connector, a housing unit, and a one-way valve. The connector can have a first port, a second port, a third port and a branched lumen that extends through each of the first, second and third ports. The housing unit can have a housing lumen that is sized and shaped to receive the third port. In some embodiments, the housing unit can further have a slot that is sized and shaped to receive the connector. The one-way valve can be sized and shaped to be received in the housing lumen.

In another embodiment, an apparatus for draining material from a stomach and infusing fluid into the stomach comprises a tubing set, a fluid reservoir, and a housing unit to connect the fluid reservoir to the tubing set. The tubing set includes a connector that has three ports and a branched lumen which connects all of the ports. The fluid reservoir consists of a deformable container which when squeezed ejects fluid from the reservoir. The housing has a housing lumen which connects the third port of the connector to the fluid container through a one-way valve and a means to occlude the fluid flow out of the first fluid port of the connector.

Methods of assembling an apparatus for draining material from a stomach and infusing fluid into the stomach are also disclosed. In one embodiment a connector is removed from a housing unit, the connector defining a first port, a second port, and a branched lumen, and the housing unit defining a housing lumen. A first tube can be connected to the first port and a second tube can be connected to the second port. The connector assembly can then be fit into the housing unit such that the housing lumen and branched lumen together form a fluid conduit, and an interface between the housing unit and the connector forms a fluid tight seal.

Methods of cleaning an apparatus for draining material from a stomach are also disclosed. In one embodiment a connector can be engaged to a housing unit. The connector can define a first port, a second port, a third port and a branched lumen. The branched lumen can have a first arm that extends through the first port, a second arm that extends through the second port and a third arm that extends through the third port. The housing unit can define a housing lumen; wherein the engaging causes the branched lumen and the housing lumen together to form a fluid conduit and causes an interface between the housing unit and the connector to form a fluid tight seal. A first tube can be occluded, the first tube defining a first tube lumen. The first tube can be engaged to the first port of the connector and the first tube lumen and the branched lumen together can form a first fluid path. A fluid reservoir having an outlet and containing a fluid can be engaged to the housing unit such that the outlet and housing lumen together form a reservoir fluid pathway. A first pressure can be exerted on the fluid reservoir, causing fluid to flow from the fluid reservoir and through the conduit. The occlusion can be removed from the first tube. A second pressure can be exerted on the fluid reservoir, wherein the second pressure on the fluid reservoir causes fluid to flow from the fluid reservoir, and through the outlet, the reservoir fluid pathway, the fluid conduit and the first tube.

BRIEF DESCRIPTION OF THE DRAWINGS

The foregoing summary, as well as the following detailed description will be better understood when read in conjunction with the appended drawings. For the purpose of illustrating the subject matter, there are shown in the drawings exemplary embodiments of the subject matter; however, the presently disclosed subject matter is not limited to the specific methods, devices, and systems disclosed. In addition, the drawings are not necessarily drawn to scale. In the drawings:

FIG. 1A is a perspective view of an apparatus for draining material from a stomach in relation to a skin port.

FIG. 1B is a perspective view of the apparatus for draining material from a stomach connected to a skin port.

FIG. 5B is a perspective view of the apparatus for draining material from a stomach showing the fluid reservoir engaged to the housing unit.

FIG. 5C is a perspective view of the apparatus for draining material from a stomach showing a clamp for occluding the first tube in an unclamped position.

DETAILED DESCRIPTION

Figure 2B:
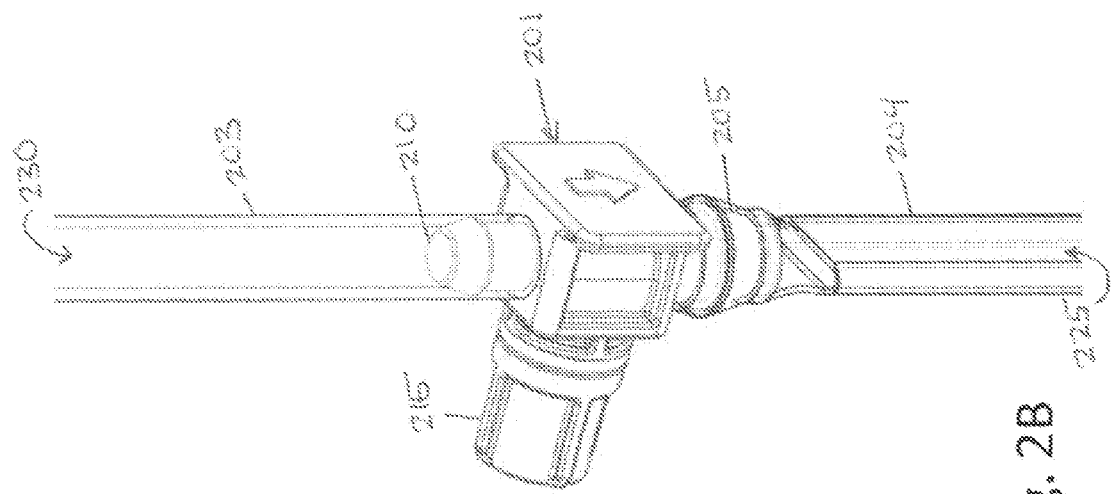
FIG. 2B is a perspective view of a connector element shown in FIG. 2A, the connector element having first and second tubes attached to the first and second ports.

The present invention may be understood more readily by reference to the following description taken in connection with the accompanying Figures and Examples, all of which form a part of this disclosure. It is to be understood that this invention is not limited to the specific products, methods, conditions or parameters described and/or shown herein, and that the terminology used herein is for the purpose of describing particular embodiments by way of example only and is not intended to be limiting of any claimed invention. Similarly, unless specifically otherwise stated, any description as to a possible mechanism or mode of action or reason for improvement is meant to be illustrative only, and the invention herein is not to be constrained by the correctness or incorrectness of any such suggested mechanism or mode of action or reason for improvement. Throughout this text, it is recognized that the descriptions refer both to the features and methods of making and using apparatuses for removal of material from a stomach, as well as the apparatuses themselves, and vice versa.

In the present disclosure the singular forms "a," "an," and "the" include the plural reference, and reference to a particular numerical value includes at least that particular value, unless the context clearly indicates otherwise. Thus, for example, a reference to "a material" is a reference to at least one of such materials and equivalents thereof known to those skilled in the art, and so forth.

When a value is expressed as an approximation by use of the descriptor "about," it will be understood that the particular value forms another embodiment. In general, use of the term "about" indicates approximations that can vary depending on the desired properties sought to be obtained by the disclosed subject matter and is to be interpreted in the specific context in which it is used, based on its function. The person skilled in the art will be able to interpret this as a matter of routine. In some cases, the number of significant figures used for a particular value may be one non-limiting method of determining the extent of the word "about." In other cases, the gradations used in a series of values may be used to determine the intended range available to the term "about" for each value. Where present, all ranges are inclusive and combinable. That is, references to values stated in ranges include every value within that range.

It is to be appreciated that certain features of the invention which are, for clarity, described herein in the context of separate embodiments, may also be provided in combination in a single embodiment. That is, unless obviously incompatible or specifically excluded, each individual embodiment is deemed to be combinable with any other embodiment(s) and such a combination is considered to be another embodiment. Conversely, various features of the invention that are, for brevity, described in the context of a single embodiment, may also be provided separately or in any sub-combination. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Finally, while an embodiment may be described as part of a series of steps or part of a more general structure, each said step may also be considered an independent embodiment in itself.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are described herein.

Referring to FIGS. 1A-1B, an apparatus 100 is configured to align with a gastrostomy tube 305 such that when the gastrostomy tube is positioned in the stomach of a patient, ingested material (semi-digested food, fluid, etc.) can drain from the stomach through the gastrostomy tube 305 and through the apparatus 100. As shown in FIGS. 1A and 1B, the apparatus 100 can comprise a first tube 204 and a second tube 203. The second tube 203 can be attached to a skin port connector 315 that can be designed to mate with a skin port 310; in some embodiments the skin port connector 315 can be locked onto the skin port 310. When the skin port connector 315 is attached and locked to skin port 310, a fluid path is formed by the gastrostomy tube 305 and the apparatus 100, including tubes 203 and 204. The apparatus 100 can include a fluid reservoir 500 for infusing fluid into the stomach through the fluid path or for rinsing the first tube 204 or the second tube 203. The fluid reservoir itself may comprise a hollow body 502 and a reservoir connector 501—see, e.g., FIG. 5B).

It should be appreciated that the term "fluid" as used herein, while generally referring to liquids, such as water, in some circumstances also includes air or other gaseous or vaporous materials. It is expected that, at times, people may squeeze air from the reservoir to clear clogs, particularly when they are in a hurry and do not want to take the time to fill the reservoir with water. Such embodiments fall within the scope of the present invention.

Figure 2A:
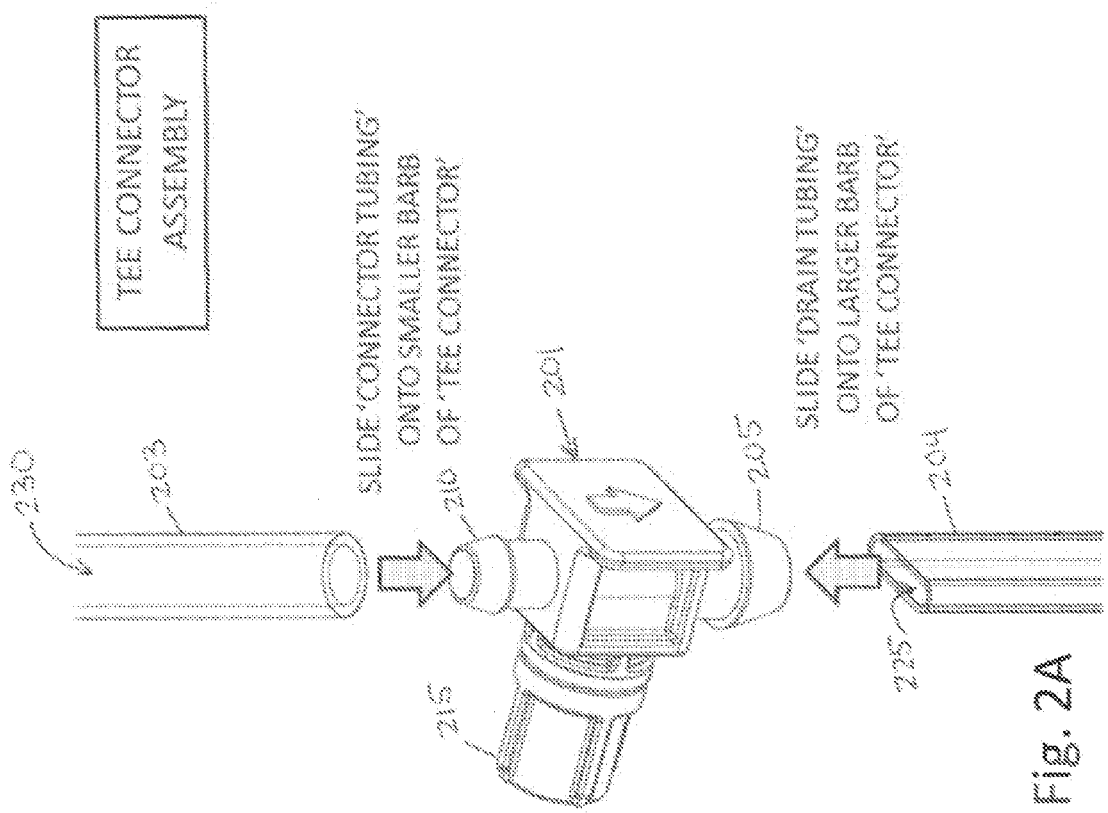
FIG. 2A is a perspective view of a connector element of an apparatus for draining material from a stomach.
Figure 3:
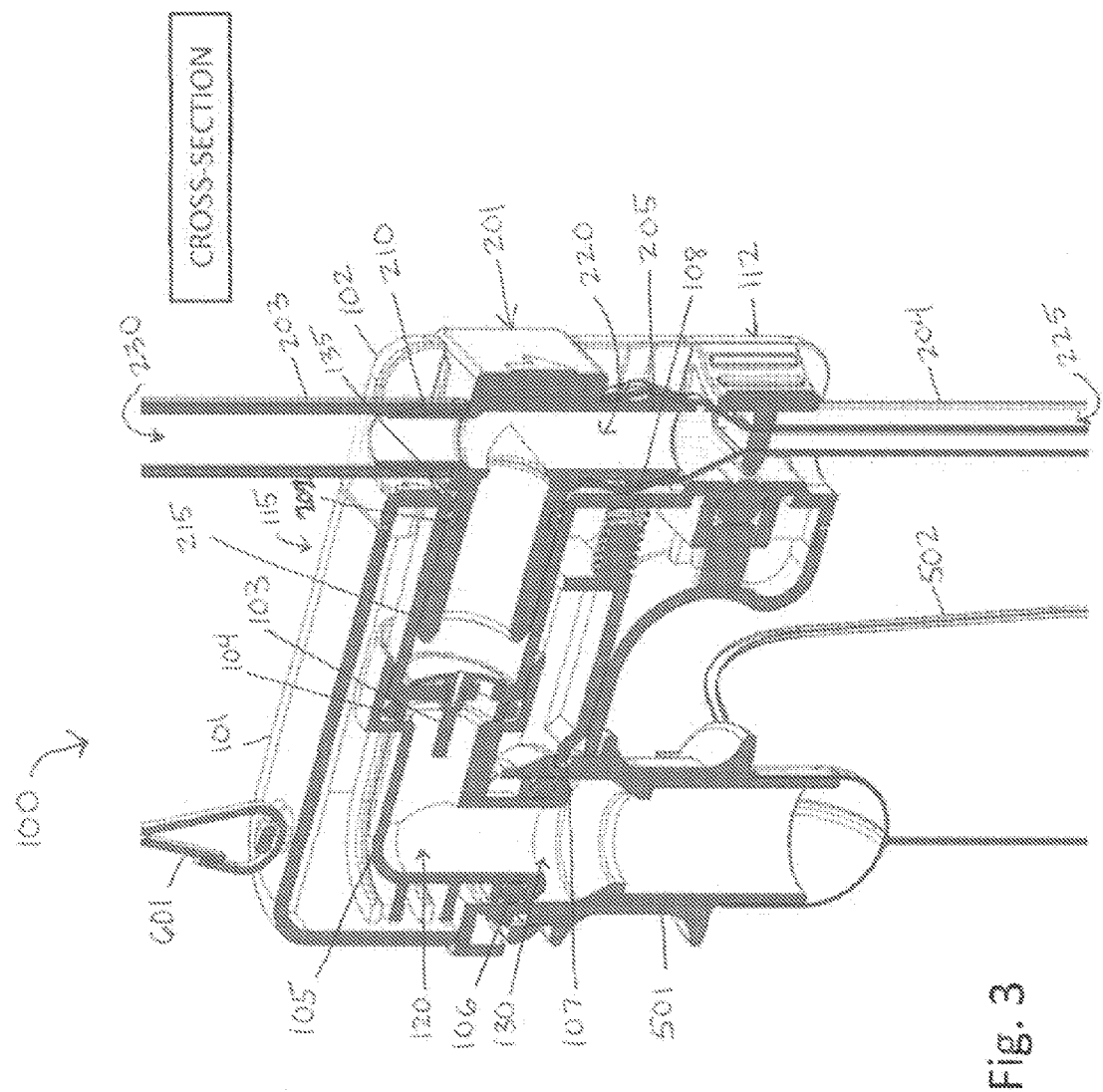
FIG. 3 is a cross-section view of an apparatus for draining material from a stomach.
Figure 4:
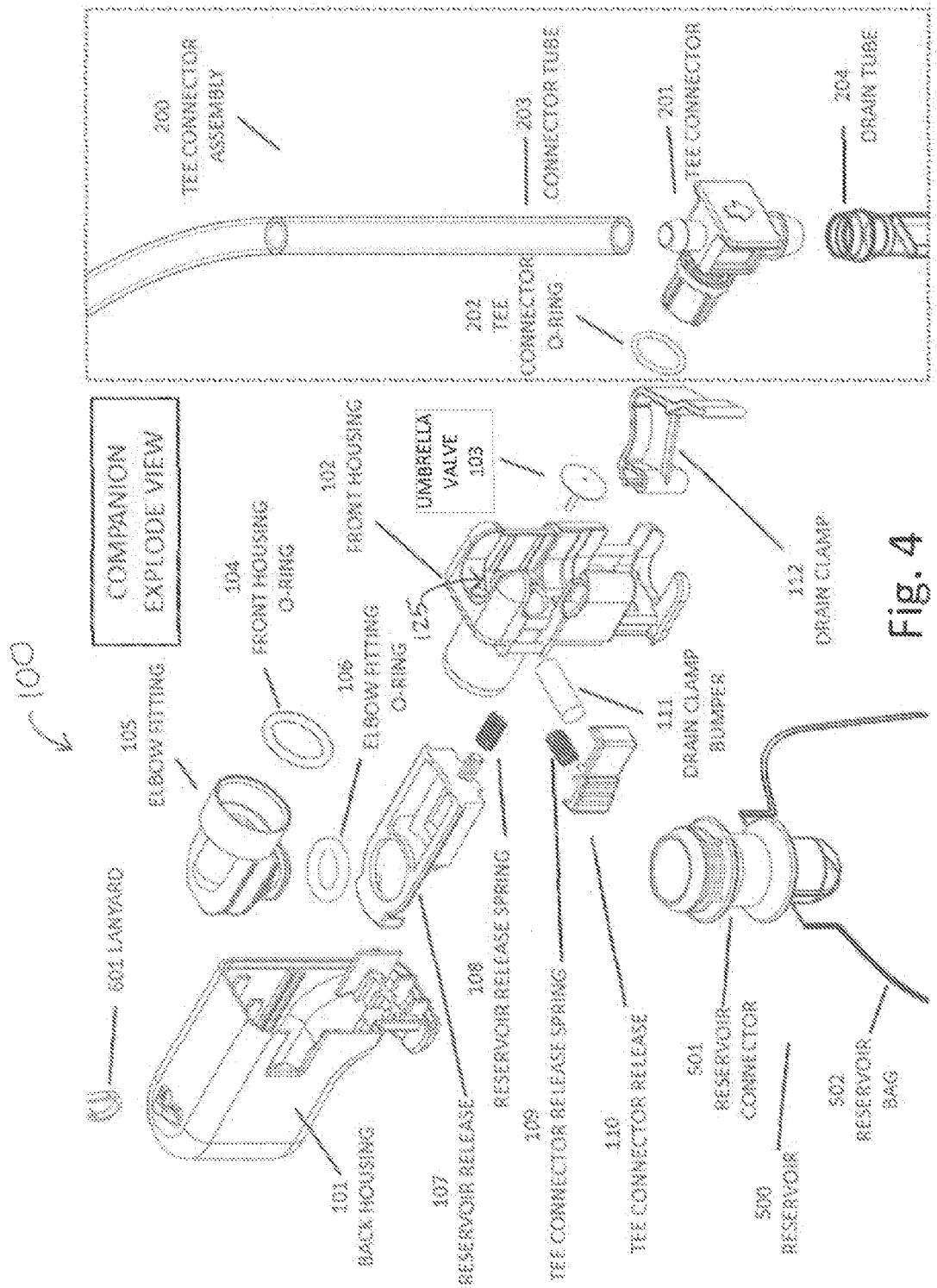
FIG. 4 is a perspective view of elements of an apparatus for draining material from a stomach according to one embodiment.

Referring now to FIGS. 2-5, the apparatus 100 can include a connector 201, a housing unit 115 (also referred to herein as "companion" or "companion body," in FIGS. 3-5) and a one way valve 103 (FIG. 3). The connector 201 can have a plurality of ports, such as a first port 205, a second port 210, and a third port 215 (see especially FIG. 2B). The connector 201 can comprise a lumen, such as a branched lumen 220 (FIG. 3). Such a branched lumen 220 can extend through each of the plurality of ports, such as the first 205, second 210, and third ports 215. The connector 201 can have a T-shape, for example where the first port 205 and second port 210 are aligned substantially along a common axis and the third port 215 is aligned perpendicular to and positioned between the first port 205 and second port 210 and can therefore be referred to as a Tee Fitting. While described here as a T-shaped connector this is but one embodiment of the connector. The shape of the connector 201 is not necessarily required to have the axes of the ports aligned or perpendicular to each other as long as the ports share a common branched lumen. Accordingly, "Y-shape" configuration may also be employed. The housing unit 115 can have a housing lumen 120. The housing lumen 120 (FIG. 3) can be straight, curved, angled, branched or any other configuration. The housing lumen 120 can extend through the housing unit such that it forms a reservoir inlet 130 and a connector inlet 135 (FIG. 3). The housing unit 115 can also have a slot 125 that is sized and shaped to receive the connector 201. The housing lumen 120 can be sized and shaped to receive the third port 215 of the connector 201. The connector 201 can engage with the housing unit 115 (FIGS. 3-5) so that part or all of the third port 215 fits within the housing lumen 120 (FIG. 3). In some embodiments the slot 125 and connector 201 are designed so that the connector 201 will only fit in the slot 125 (FIG. 5B) in a particular, pre-selected orientation. This feature can be advantageous if the tubing connected to the first port and second port are of different sizes, wall thicknesses, or materials. For example, the tube connected to the second port may be a more kink-resistant, thick-walled silicone rubber tube than the tube connected to the second port which undergoes less bending during use. While the one-way valve 103 is generally described herein as an umbrella valve, this is but one embodiment, and the valve can be any type of valve that permits the flow of fluid in one direction and prevents the flow of fluid in the opposite direction, such as a trumpet valve, a ball valve, a duck-bill valve, or an umbrella valve. The one-way valve 103 (FIG. 4) can be sized and shaped to fit within the housing lumen. In some embodiments the one way valve is positioned to permit fluid to flow in the direction from the reservoir inlet 130 toward the connector inlet 135 and to prevent fluid from flowing in the direction from the connector inlet 135 to the reservoir inlet 130 (FIG. 3). Preferably, the one-way valve is positioned to permit fluid to flow in the direction from the reservoir inlet 130 toward the connector inlet 135 thereby allowing fluid to flow from the fluid reservoir 502 through the second tube 203 into the patient's stomach, or from the fluid reservoir 502 through both the first tube 504 and the second tube 203 for clearing obstructions or cleaning. Positioning the one-way valve so that fluid cannot flow from the connector inlet 135 toward the reservoir inlet will also prevent material that is drained from the stomach from passing from the second tube 203 to the fluid reservoir 502.

Referring to FIGS. 2A/B, 3, and 5A, the apparatus can include a first tube 204 having a first tube lumen 225 that is sized and shaped to connect to the first port 205. The first tube 204 can connect to the first port 205 by receiving the first port 205 in the first tube lumen 225 (see FIGS. 2A/B). Alternatively the first port 205 can receive the first tube lumen 225 in the branched lumen 220 extending through the first port 205. When the first tube 204 is connected to the first port 205 the first tube lumen 225 and the branched lumen 220 form a conduit through which fluid can pass. The apparatus can also include a second tube 203 having a second tube lumen 230 that is sized and shaped to connect to the second port 210. The second tube 203 can connect to the second port 210 by receiving the second port 210 in the second tube lumen 230. Alternatively the second port 210 can receive the second tube lumen 230 in the branched lumen 220 extending through the second port 210. When the second tube 203 is connected to the second port 210 the second tube lumen 230 and the branched lumen 220 form a conduit through which fluid can pass.

Referring now to FIGS. 3, 4, and 5A-C, the housing unit 115 can be comprised of a back housing 101 and a front housing 102. The housing unit 115 can also include one or more tubular fittings, such as elbow fitting 105, which together with the back housing 101 and the front housing 102 define lumen 120. The housing unit can further comprise one or more gaskets, such as O-rings 104 and 106, which can be made of an elastomeric material and can form a fluid tight seal between individual elements of the housing unit. Alternatively the housing unit 115 can be made of a single element having a lumen therein.

Some embodiments contain a fixture within the back housing 101 onto which a lanyard 601 or neckstrap may be fastened. The incorporation of such a lanyard/neck strap is important for the ease of use of the device, since it supports the apparatus during therapy, thus freeing up both hands of the patient to manipulate the device. In preferred embodiments, the device is designed to make it easy for the lanyard to be removed for cleaning purposes.

Still referring to FIG. 4, the apparatus 100 can further comprise a fluid reservoir 500 for holding a fluid. The fluid reservoir 500 can have a hollow body 502, for example a bag or a bottle. The reservoir body 502 can be made of a flexible material. In some embodiments the reservoir body 502 is constructed of two layers of welded flexible film. The reservoir body 502 can then be flattened and folded or rolled when not in use. The fluid reservoir 500 can also have a reservoir connector 501 for engaging the housing unit 115. The reservoir connector 501 can be permanently affixed to the reservoir body 502 or can be detachable from the reservoir body 502. The reservoir connector 501 can include a groove, threading, lip, or other structure capable of engaging the housing unit 115. In other embodiments, the reservoir comprises a bottle, or other reservoir body, with an accompanying pump that is capable of forcing air out of the reservoir.

As shown in FIG. 4, the housing unit 115 can include a reservoir locking device for holding a fluid reservoir 500 to the housing unit 115, for example by spring-tension. In an embodiment, a reservoir locking device can include a reservoir release 107. The reservoir release 107 can engage a groove or a lip on the reservoir connector 501. The reservoir locking device can also include a reservoir release spring 108 that can exert a biasing force on the reservoir release 107. The reservoir 500 can be locked to the reservoir release 107 by pushing the reservoir connector 501 into the lumen 120 of housing unit 115 until the reservoir 500 is positioned such that the reservoir release spring 108 pushes the reservoir release 107 into a groove on the reservoir connector 501. The reservoir 500 can be released by simultaenously disengaging the reservoir release 107 from the reservoir connector 501 and pulling the reservoir away from the housing unit 115. The reservoir release 107 can be disengaged from the reservoir connector 501, for example, by having a portion of the reservoir release 107 at the opposite end of the reservoir release 107 from the reservoir release spring 108, or a button connected to the reservoir release 107 or the reservoir release spring 108, accessible from the outside of the housing unit 115 so that depression of the button or reservoir release 107 compresses the reservoir release spring 108 and disengages the reservoir release 107 from the reservoir connector 501. FIG. 5B illustrates an embodiment where the reservoir 500 is engaged with the housing unit 115. The solid arrow indicates that the reservoir release button will extend away from the housing unit 115 and the reservoir release 107 will snap into locked position when the reservoir connector 501 reaches the proper engagement depth.

Figure 5A:
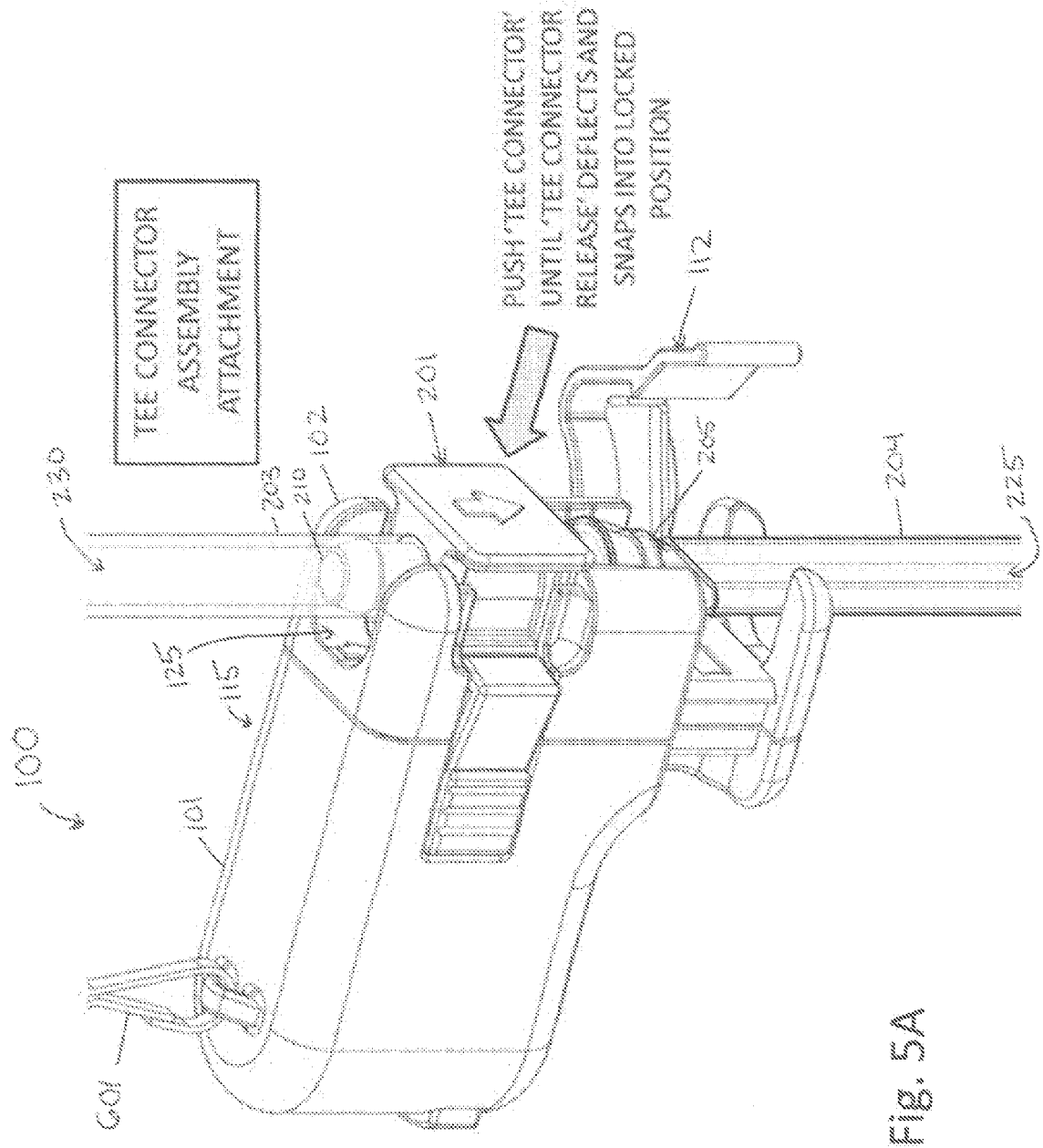
FIG. 5A is a perspective view of an apparatus for draining material from a stomach showing the connector engaged to the housing unit.

The housing unit 115 can include a locking device that can hold the connector 201 to the housing unit 115, such as by spring-tension. In some embodiments, the locking device can be made of a connector release 110 and connector release spring 109. As the connector 201 is pushed into the slot 125, the connector 201 can deflect the connector release spring 109 until the connector 201 is fully engaged with the housing unit 115 and the connector release spring 109 holds the connector 201 in place. The connector 201 can be removed from the housing unit 115 by simultaneously depressing a button (such as a rocker) connected to the connector release spring 109 and pulling the connector 201 away from the housing unit 115. FIG. 5A illustrates the connector 201 positioned in slot 125 of housing unit 115 but not fully engaged with the housing unit 115. The solid arrow indicates that connector 201 can be fully engaged with the housing unit 115 and locked in place by pushing the connector 201 until the connector release 110 deflects and continuing to push the connector 201 until it snaps into the locked position.

As shown in FIGS. 1, 3, and 5A-B, the apparatus 100 can also include a clamp 112 for occluding the first tube lumen 225. FIG. 5C illustrates an embodiment of apparatus 100 including a clamp 112, where the clamp 112 is in an open position and not occluding the first tube lumen 225. The solid arrow indicates that the clamp 112 can be rotated until it is in a locked position, indicating that the first tube lumen 225 is occluded. It may be desirable to lock the drain clamp 112 and so close the fluid path through the first tube 204 in order to direct fluid from the fluid reservoir into the second tube 203 and into the stomach. It may also be desirable to lock the drain clamp 112 and so close the fluid path through the first tube 204 in order to direct fluid from the fluid reservoir into the second tube 203 to rinse the second tube 203 after it has been used to drain material from the stomach.

In an illustrative embodiment, and with reference to FIG. 4, an apparatus 100 can have Drain Tube (204) and Connector Tube (203) connected via a removable 3-way Tee Connector (201). The third port 215 of Tee Connector (201) can connect to a bore 120 in the Companion body 115 with an O-ring seal 202. When the Tee Connector (201) is attached to the Companion body 115, Tee Connector Release (110) can be used to secure it to the Companion body 115. At the other end of the bore 120 in the Companion body 115 there can be an Umbrella Valve (103). An Umbrella Valve (103) is a one-way check valve, which can be mounted on a surface through a small hole, which also can have additional openings located at strategic areas within, for example under the dome of, the profile of the Umbrella Valve (103) for allowing fluids to flow into the adjacent chamber. The design of the Umbrella Valve (103) is a thin circular dome or umbrella-like shape that seals against fluid flow in one direction and lets fluid pass through the other direction with a very low cracking pressure. The opening on the other side of the Umbrella Valve (103) can be connected to the Reservoir (500) via an Elbow Fitting (105). The Reservoir (500) can connect to the Companion body 115 by means of an easily detachable reservoir Connector (501). An O-ring mounted to the Elbow Fitting (105) can create a seal between the Reservoir Connector (501) and Elbow Fitting (105) when connected. When the Reservoir (500) is squeezed it can create a pressure in excess of the cracking pressure of the Umbrella Valve (103) which results in water flow through the bore 120 of the Companion body 115, into the Tee Connector (201) and beyond. The slot 125 can include channels on the either side of the Tee Connector (201) for Drain Tube (204) and the Connector Tube (203) to rest within the profile of the Companion body 115. There is an L-shaped Drain Clamp (112) for clamping and occluding Drain Tube (204).

Referring now to FIG. 1, The skin port connector (315) can be located at the distal end of the Connector Tube (203), that is, the end of the second tube (203) nearest the body of the patient. The distal end of the Connector Tube (203) can be connected to the gastrostomy tube (305) through Skin Port Valve and Skin Port Flange (310).

Advantages of the various features of the present invention can be understood with reference to FIGS. 2-4. Apparatuses of the invention can be smaller and lighter than previous designs. In an embodiment of the invention, an apparatus can use an Umbrella Valve (103) instead of duckbill valve as a one-way check valve. In this design, an Umbrella Valve (103) can provide better features than the duckbill valve in the following areas: (1) better flow rate for infusion of water while not allowing any flow in the reverse direction, thus, reducing infusion time; (2) infusion requires less effort by the patient in exerting pressure on the reservoir bag (502); (3) faster infusion enables better cleaning the fluid paths; (4) faster fluid flow reduces possibility of occlusion and (5) it is easier to clean partially-digested food particles from the domed surface of the umbrella valve without damaging the seal. Designs of the invention employ a simplified fluid path that can be easily disassembled and reassembled by the patient for cleaning and maintenance purposes. Design of the invention enables the patient to remove the Tee Fitting sub-assembly (200) with associated tubing (203, 204) from main structure of device (115). The Tee Fitting sub-assembly (200) can be further dissembled by detaching drain (204) and connector tubes (203) from barb connections (205, 210) of Tee Fitting. The connector may also be molded from a transparent, tinted, or translucent plastic to allow the user to visually inspect the branched lumen within the connector. Therefore, in designs of the invention, no semi-digested food can remain inside the device that cannot easily be noticed, enabling thorough cleaning of the device after the procedure, and preventing the possibility of generating foul odor. An additional advantage of the present invention having a removable connector 201 is that the Tee Connector (201) can be keyed to the housing body 115 to prevent reverse installation of Connector Tube (203) and Drain Tube (204) orientations. In an alternative embodiment, the entire Tee-fitting tubing subassembly may be supplied as a pre-assembled disposable. This is particularly advantageous for situations such as dining out, where it may be inconvenient to clean the tubing set. This would also allow less expensive, lower durable materials to be used for the tubing and connector. A push-to-connect Reservoir (500) attachment system is easier to use and does not require radial alignment of Reservoir Connector (501) to housing 115 to engage locking mechanism. A single button release feature may be used to un-lock the Reservoir (500) from housing 115. The Reservoir (500) is constructed of two layers of welded flexible film which, when empty, can be flattened and rolled up, requiring minimum space for storage between uses. Such a Reservoir (500) is more durable since it can be manufactured from a stronger and thicker material. The Reservoir Connector (501) can be welded to the film of the Reservoir Bag (502).

The apparatus can be assembled before aspiration therapy, or draining ingested material from a patient's stomach and infusing fluid into the stomach. First the Tee Connector (201) is removed from housing 115. The Connector Tube (203) is attached to the proper barbed fitting (210) of the Tee Connector (201). Connect Drain Tube (204) to the proper barb fitting (205) of the Tee Connector (201). The Tee Connector (201) is inserted into the housing 115, making sure O-ring is in place and not twisted and the Tee Connector (201) is secured by the Tee Connector Release (110). The Drain Clamp (112) is rotated closed to occlude Drain Tube (204). After filling the Reservoir (500) with water, it is connected to the bottle connector or reservoir locking device by pushing up until it snaps in place. The skin port connector 315 is connected to the Skin Port Valve 310 of the patient and latched by pushing the lever on the skin port Connector 315 until a click is heard, confirming it is properly connected. The patient is then ready for the aspiration therapy.

Apparatuses of the invention can be used to perform aspiration therapy, and methods of assembling an apparatus for draining material from a stomach and infusing fluid into the stomach are also considered within the scope of the present invention. In one embodiment a connector is removed from a housing unit, the connector defining a first port, a second port, and a branched lumen, and the housing unit defining a housing lumen. A first tube can be connected to the first port and a second tube can be connected to the second port. The connector assembly can then be fit into the housing unit such that the housing lumen and branched lumen together form a fluid conduit, and an interface between the housing unit and the connector forms a fluid tight seal. While it is somewhat easier to attach the tubing with the connector out of the housing, the tubing can be attached regardless of whether the connector is inserted in the housing or removed. Regardless, this isn't necessarily an advantage. What is advantageous is that the tubing set with the connector can be treated as a single unit. The user will typically keep this tubing set assembled and ready to use or clean it as a unit.

When used for aspiration therapy, the housing 115 connects to the gastrostomy tube 305 via the skin port Connector 315 and the Skin Port valve 310. It provides a passage for aspiration of the semi-digested food out of the patient's stomach. It provides the means for infusing water into the patient's stomach to improve aspiration. It provides a simpler way of cleaning the housing 115 and associated connector 201 and tubing 203, 204 after the procedure.

The following is an example method of aspiration: After the assembled apparatus is connected to the patient through a skin port connector 315, the Drain Tube (204) can be placed over a toilet, bucket, or other removal system for discharging aspirated semi-digested food and fluid from the patient. Unclamping the Drain Tube (204) by releasing the Drain Clamp (112) starts aspiration. Semi-digested food can flow by gravitation and siphon from the gastrostomy tube 305, through the Skin Port valve, and the skin port connector 315 into the Connector Tube (203). Then it can flow into the Tee Connector (201). The Umbrella check valve (103) downstream of the third port 215, does not allow the fluid to pass through into the Reservoir (500). The aspirating semi-digested food can only flow into the Drain Tube (204) for discharge into the toilet.

The addition of water into the stomach can increase the pressure inside the stomach and dilute the contents within the stomach of the patient and improve aspiration. This can be done if and when aspiration stops even when connected to the apparatus 100 with Drain Tube (204) open. The following is an example procedure for infusing water: Occlude the Drain Tube (204), for example, by clamping using the Drain Clamp (112). This blocks the infusing water from flowing into the Drain Tube (204). Squeezing the Reservoir (500) creates pressure forcing water to flow out of the Reservoir, past the Umbrella valve and into the third port of the connector. Since the drain tube is occluded by the Drain Clamp, the water is forced through the second port into the Connector Tube (203), gastrostomy tube (305) and into the stomach clearing any clogs by the force of the water pressure. This additional volume of water in the patient's stomach increases the pressure inside the patient's stomach to restart aspiration.

Methods of cleaning an apparatus for draining material from a stomach are also disclosed. In one embodiment a connector can be engaged to a housing unit. The connector can define a first port, a second port, a third port and a branched lumen. The branched lumen can have a first arm that extends through the first port, a second arm that extends through the second port and a third arm that extends through the third port. The housing unit can define a housing lumen; wherein the engaging causes the branched lumen and the housing lumen together to form a fluid conduit and causes an interface between the housing unit and the connector to form a fluid tight seal. A first tube can be occluded, the first tube defining a first tube lumen. The first tube can be engaged to the first port of the connector and the first tube lumen and the branched lumen together can form a first fluid path. A fluid reservoir having an outlet and containing a fluid can be engaged to the housing unit such that the outlet and housing lumen together form a reservoir fluid pathway. A first pressure can be exerted on the fluid reservoir, causing fluid to flow from the fluid reservoir and through the conduit. The occlusion can be removed from the first tube. A second pressure can be exerted on the fluid reservoir, wherein the second pressure on the fluid reservoir causes fluid to flow from the fluid reservoir, and through the outlet, the reservoir fluid pathway, the fluid conduit and the first tube.

The following is a method for cleaning the apparatus 100 after the procedure is over: Remove the apparatus 100 from the patient by releasing the skin port Connector 315 from the Skin Port valve 310. Occlude the Drain Tube 204, such as by closing the Drain claim 112. Squeezing the Reservoir 500 forces water through the Umbrella Valve 103 into the Tee Connector 201. Since the Drain Tube 204 is clamped, water will flow through the Tee Connector 201 cleaning the skin port connector 315, the Connector Tube 203 and part of the Tee Connector 201. Next, occlude the Connector Tube 203 by blocking the Connector port 210 or by pinching the Connector Tube 203 closed. Unclamp the Drain Tube 204 by releasing the Drain Clamp 112. Squeeze the Reservoir 500 to force water through the Umbrella Valve 103 into the Tee Connector 201. Since, the water cannot flow through the occluded Connector Tube 203; it will flow through the Drain Tube 204 to discharge into the toilet. This will remove any food particles from the Drain Tube 204 and part of the Tee Connector 201.

It is to be understood that while the invention has been described in conjunction with the preferred specific embodiments thereof, that the foregoing description and the examples that follow are intended to illustrate and not limit the scope of the invention. It will be understood by those skilled in the art that various changes may be made and equivalents may be substituted without departing from the scope of the invention, and further that other aspects, advantages and modifications will be apparent to those skilled in the art to which the invention pertains. In addition to the embodiments described herein, the present invention contemplates and claims those inventions resulting from the combination of features of the invention cited herein and those of the cited prior art references which complement the features of the present invention. Similarly, it will be appreciated that any described material, feature, or article may be used in combination with any other material, feature, or article, and such combinations are considered within the scope of this invention.

What is claimed is:

1. An apparatus (100) for draining material from a stomach and infusing fluid into the stomach comprising:
    (a) a housing unit (115) comprising a back housing (101) and a front housing (102), said housing unit (115) having a housing lumen (120) and said front housing (102) having a slot 125; the housing unit further comprising a spring-tensioned connector locking device, the locking device comprising a connector release (110) and a connector release spring (109) configured such that, as a removable tubing connector (201) is pushed into a slot (125), the connector (201) can deflect the connector release spring (109) until the connector (201) is fully engaged with the housing unit (115) and the connector release spring (109) holds the connector (201) in place, and
    (b) a one-way valve (103) that is sized and shaped to be received in the housing lumen (120); wherein
    the removable tubing connector (201) comprises a first port (205), a second port (210), and a third port (215), said connector (201) further comprising a branched lumen (220) having a first arm that extends through the first port (205), a second arm that extends through the second port (210), and a third arm that extends through the third port (215); and wherein
    said slot (125) is sized and shaped to reversibly engage the removable tubing connector (201) only in a preselected orientation and wherein said housing lumen (120) is sized and shaped to receive the third port (215) of the removable tubing connector (201).

2. The apparatus according to claim 1, further comprising a first tube (204) having a first tube lumen (225), the first tube lumen (225) being sized and shaped for receiving the first port (205).

3. The apparatus according to claim 2, further comprising a second tube (203) having a second tube lumen (230), the second tube lumen (230) being sized and shaped for receiving the second port (210).

4. The apparatus according to claim 2, further comprising a clamp (112) for occluding the first tube lumen (225).

5. The apparatus according to claim 1, further comprising a fluid reservoir (500).

6. The apparatus according to claim 1, the removable tubing connector (201) defining a T-shape or a Y-shape.

7. The apparatus according to claim 1, the one-way valve (103) being a trumpet valve, a ball valve, a duck-bill valve, or an umbrella valve.

8. The apparatus according to claim 5, the housing unit further comprising a fluid reservoir locking device for holding the fluid reservoir (500) in fluid communication with the housing lumen (120) of the housing unit (115) by spring tension, wherein the reservoir locking device includes a reservoir release (107) for engaging a groove or a lip on a reservoir connector (501).

9. The apparatus according to claim 8, further comprising a fluid reservoir (500) having a hollow body (502).

10. The apparatus according to claim 9, the fluid reservoir (500) comprising a flexible material.

11. A method of assembling an apparatus (100) for draining material from a stomach and infusing fluid into the stomach, the apparatus comprising:
    (a) a housing unit (115) comprising a back housing (101) and a front housing (102), said housing unit (115) having a housing lumen (120) and wherein said front housing (102) has a slot (125) that is sized and shaped to reversibly engage a removable tubing connector (201) only in a preselected orientation, the removable tubing connector (201) having a first port (205), a second port (210), and a third port (215), and wherein said housing lumen (120) is sized and shaped to receive the third port (215) of the removable tubing connector (201);
    (b) a one-way valve (103) that is sized and shaped to be received in the housing lumen (120);
    (c) the removable tubing connector (201) further comprising a branched lumen (220) having a first arm that extends through the first port (205), a second arm that extends through the second port (210), and a third arm that extends through the third port (215);
    (d) a first tube (204) having a first tube lumen (225), the first tube lumen (225) being sized and shaped for receiving the first port (205); and
    (e) a second tube (203) having a second tube lumen (230), the second tube lumen (230) being sized and shaped for receiving the second port (210),
    the method comprising:
    removing the removable tubing connector (201) from the housing unit (115);
    connecting the first tube (204) to the first port (205);
    connecting the second tube (201) to the second port (210);
    fitting the removable tubing connector (201) into the front housing (102) of the housing unit (115) such that the housing lumen (120) and branched lumen (220) together form a fluid conduit and an interface between the housing unit (115) and the removable tubing connector (201) that forms a fluid tight seal.

12. A method of cleaning an apparatus (100) for draining material from a stomach and infusing fluid into the stomach, the apparatus comprising:
    (a) a housing unit (115) comprising a back housing (101) and a front housing (102), said housing unit (115) having a housing lumen (120) and wherein said front housing (102) has a slot (125) that is sized and shaped to reversibly engage a removable tubing connector (201) only in a preselected orientation, the removable tubing connector (201) having a first port (205), a second port (210), and a third port (215), and wherein said housing lumen (120) is sized and shaped to receive the third port (215) of the removable tubing connector (201);

(b) a one-way valve (103) that is sized and shaped to be received in the housing lumen (120);

(c) the removable tubing connector (201) further comprising a branched lumen (220) having a first arm that extends through the first port (205), a second arm that extends through the second port (210), and a third arm that extends through the third port (215);

(d) a first tube (204) having a first tube lumen (225), the first tube lumen (225) being sized and shaped for receiving the first port (205); and (e) a second tube (203) having a second tube lumen (230), the second tube lumen (230) being sized and shaped for receiving the second port (210), the method comprising:

engaging the removable tubing connector (201) to a housing unit (115); wherein the engaging causes the branched lumen (220) and the housing lumen (120) to fit together to form a fluid conduit and the engaging causes an interface between the housing unit (115) and the connector (201) to form a fluid tight seal;

occluding the first tube (204), the first tube (204) being engaged to the first port (205) of the connector (201), the first tube lumen (225) and the branched lumen (220) together forming a first fluid path;

engaging a fluid reservoir (500) having an outlet (501) and a hollow body (502) containing a fluid to the housing unit (115), such that the outlet (501) and housing lumen (120) together form a reservoir fluid pathway;

exerting a first pressure on the fluid reservoir (500), causing fluid to flow from the fluid reservoir (500) and through the conduit;

removing the occlusion from the first tube (204); and exerting a second pressure on the fluid reservoir (500), wherein the second pressure on the fluid reservoir (500) causes fluid to flow from the fluid reservoir (500), and through the outlet (501), the reservoir fluid pathway, the fluid conduit and the first tube (204).

13. The method according to claim 12, further comprising occluding the second tube (203), the second tube being engaged to the second port (210) of the connector (201), the second tube lumen (230) and the branched lumen (220) together forming a second fluid path.

14. The method according to claim 12, further comprising disposing a fluid within the fluid reservoir (500).

15. The method according to claim 12, wherein the engaging a fluid reservoir (500) step comprises locking the fluid reservoir (500) to the housing unit (115) with spring tension.

\* \* \* \* \*